(12) United States Patent
Ogura

(10) Patent No.: US 6,335,452 B2
(45) Date of Patent: Jan. 1, 2002

(54) 1-SUBSTITUTED 2,5-DITHIENYL PYRROLE DERIVATIVES AND FILM-FORMING MATERIALS

(75) Inventor: Katsuyuki Ogura, Narashino (JP)

(73) Assignee: Chiba University (JP)

( * ) Notice: Subject to any disclaimer, the term of this patent is extended or adjusted under 35 U.S.C. 154(b) by 0 days.

(21) Appl. No.: 09/803,019

(22) Filed: Mar. 12, 2001

(51) Int. Cl.⁷ ............................................. C07D 409/04
(52) U.S. Cl. ...................................... 548/527
(58) Field of Search ......................................... 548/527

(56) References Cited

PUBLICATIONS

Meeker et al. (1998): Macromolecules, vol. 31, 2943–2946.*

* cited by examiner

*Primary Examiner*—Jane C. Oswecki
*Assistant Examiner*—Golam M. M. Shameem

(74) *Attorney, Agent, or Firm*—Burns, Doane, Swecker, & Mathis, L.L.P.

(57) ABSTRACT

A 1-substituted 2,5-dithienylpyrrole derivative having the following formula (I).

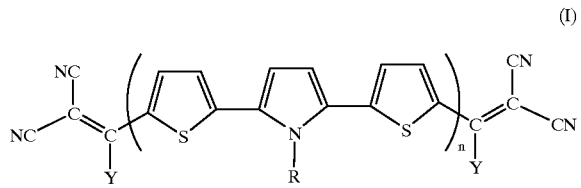

in which R is hydrogen, a substituted or non-substituted alkyl group, or a substituted or non-substituted aromatic group, Y is hydrogen or cyano group, it can be involved the case that one of Ys may be hydrogen and the other may be cyano group, and n is an integer of 1 to 3. The derivative is used for forming films.

1 Claim, 3 Drawing Sheets

(3 of 3 Drawing Sheet(s) Filed in Color)

1-SUBSTITUTED 2,5-DITHIENYL PYRROLE DERIVATIVES AND FILM-FORMING MATERIALS

BACKGROUND OF THE INVENTION

1. Field of the Invention

The present invention relates to organic materials with π-electron systems, and particularly to 1-substituted 2,5-dithienylpyrrole derivatives that conform stable molecular aggregates and film-forming materials.

2. Related Art Statement

The compounds forming films with metallic colors have been widely utilized as the materials forming metallic color films. Up to now, the films are commonly colored with various kinds of colorants based on powder of a metal such as aluminum. However, the formation of metal-lustrous color-possessing films from organic materials only and without a metal will be able to provide metallic color-possessing films that do not have a harmful influence on the environment, because the films can be disposed of by burning.

It has been formerly known that polymer compounds having the π-electron systems such as polyacetylene and polydiacetylene exhibit metallic luster when doped with iodine or the like. Compounds, such as polysulfur nitride, in which radicals continue, exhibit metallic luster.

However, the polymer compounds such as polyacetylene and polydiacetylene are unstable in air not only even when doped but also even when not doped. Thus, such polymer compounds are not practical.

The compounds, in which the radicals continue, such as polysulfur nitride continue are more unstable in air.

In order that the above compounds may be used as film-forming materials, handling is facilitated by improving solubiliity in an organic solvent during the production. However, the compounds are required to afford less solubility in the solvent after the formation of the film. However, a film-forming material having such properties has not been found up to now.

SUMMARY OF THE INVENTION

It is an object of the present invention to provide organic compounds being stable in air and exhibiting a metallic lusters.

It is another object of the present invention to provide film-forming materials containing the above organic compounds.

In order to solve the above problems, the present inventor noted low molecular weight compounds with nelectron systems which are stable and easy to handle, and tackled with a problem for the production of a metallic color through forming a stable aggregate by self-assembling to realize an intermolecular interaction of electron systems. As a result, the following compounds according to the present invention were found out. The derivatives according to the present invention are 1-substituted-2,5-dithienylpyrrole derivatives having the following formula (I).

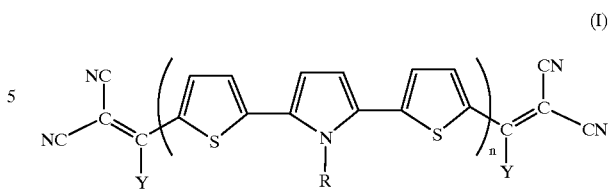

(I)

in which R is hydrogen, a substituted or non-substituted alkyl group, or a substituted or non-substituted aromatic group, Y is hydrogen or cyano group, it is also involved the case that one of Ys may be hydrogen and the other cyano group, and n is an integer of 1 to 3.

The present invention is also directed to a film-forming material comprising the 1-substituted 2,5-dithienyl pyrrole derivative.

These and other objects, features and advantages of the present invention will be appreciated upon reading the following description of the invention in conjunction with the attached drawings, with the understanding that some modifications, variations and changes of the invention could be easily made by a skilled person in the art to which the invention pertains.

BRIEF DESCRIPTION OF THE INVENTION

The file of this patent contains at least one drawing executed in color. Copies of this patent with color drawings (s) will be provided byd the Patent and Trademark Office upon request and payment of the necessary fee.

For better understanding of the invention, reference is made to the attached drawings, wherein:

FIGS. 1(A), 1(B) and 1(C) are photographs of crystals of 1-phenyl 2, 5-bis[5-(tricyanoethenyl)-2-thienyl]pyrrole as a compound in Example 1, which were recrystallized from DMF, dried under vacuum and recrystallized from acetone, respectively;

DETAILED DESCRIPTION OF THE INVENTION

Figure 1A:
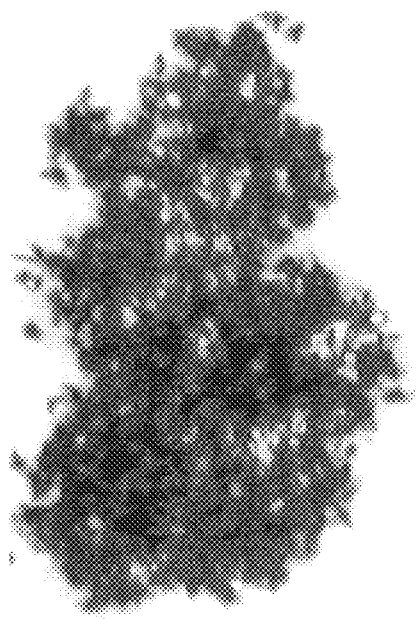
Figure 1B:
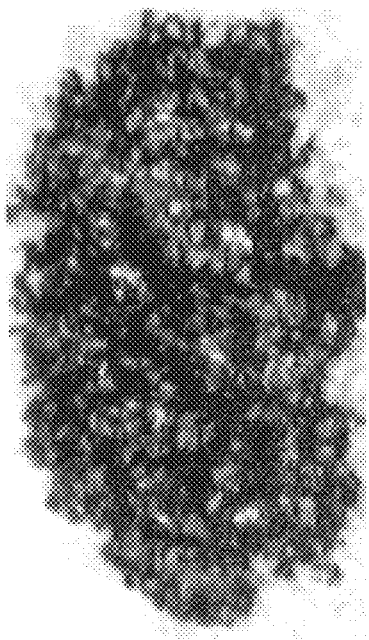
Figure 1C:
Figure 2:
FIG. 2 is a photograph of a crystal of 1-(4-chlorophenyl)-2,5-bis [5-(tricyanoethenyl)-2-thienyl]pyrrole as a compound in Example 5 (recrystallized from DMF)
Figure 3:
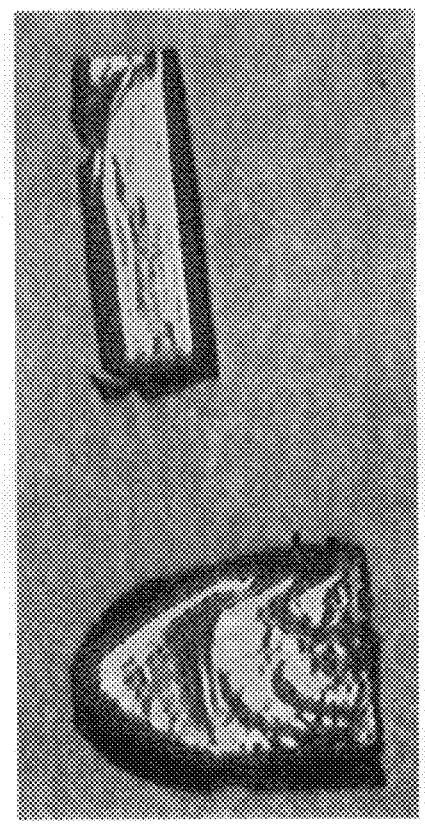
FIG. 3 is a photograph of crystals of 1-(2-bromophenyl)-2,5-bis [5-(tricyanoethenyl)-2-thienyl] pyrrole as a compound in Example 7 (recrystallized from acetone)
Figure 4:
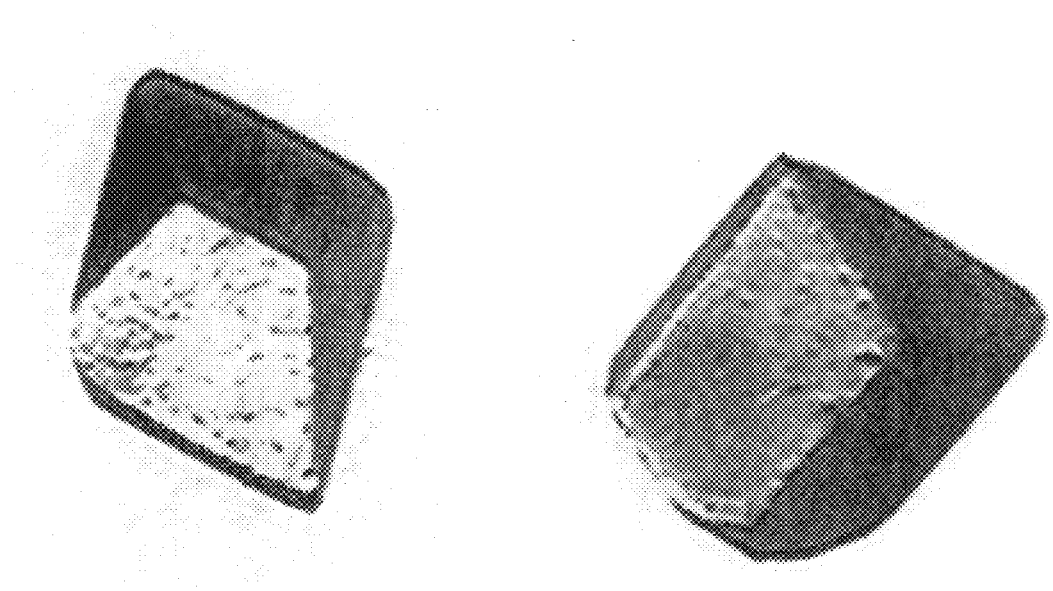
FIG. 4 is a photograph of crystals of 1-(2-bromophenyl)-2,5-bis [5-(tricyanoethenyl)-2-thienyl] pyrrole as the compound in Example 7 (recrystallized from acetone).

The file of thi spatent contains at least one drawing executed in color. Copies of this patent with color drawing (s) will be provided by the Patent and Trademark Office upon request and payment of the necessary fee.

The present inventors discovered that, since the above-mentioned 1-substituted 2,5-dithienylpyrrole derivatives have high durability, they can be used for coating materials, organic metal plating agents, organic semiconductors, organic EL materials, etc.

The 1-substituted 2,5dithienylpyzrole derivatives according to the present invention shown in the formula (I) are compounds exhibiting metallic colors in the state of crystals or thin films. These compounds can be dissolved in general organic solvents such as acetone, benzene, chloroform, tetra-hydrofuran, N, N-dimethylformamide (DMF), and toluene, and then easily recrystallized from such organic solvents. When the solution of the compound mentioned above in an organic solvent is allowed to stand at room temperature, crystals having a metallic color are deposited. Since the compounds according to the present invention are stable against heat, crystals can be also obtained by heating them above their melting points to melt and then cooling of the melt gradually to room temperature.

When a solution of the above compound in an organic solvent is spread and coated onto an appropriate base material and then dried, a film having metallic luster can be easily formed. Since the compounds according to the present invention are extremely stable against heat, such films can be also formed by utilizing vacuum evaporation or spin coating.

In the above-mentioned formula (I), R is hydrogen, a substituted or non-substituted alkyl group (containing a cycloalkyl group), a substituted or non-substituted aromatic group, a formyl group, an acyl group, an alkoxycarbonyl group or an alkenyl group. The alkyl group constituting R is preferably a C1–C30 alkyl group, and particularly preferably a C1–C18 alkyl group. As substituting groups of the alllyl group, C1–C18 alkoxy groups, aromatic groups such as a phenyl group, a naphtyl group, a benzothienyl group, an indolyl group and a pyridyl group, a phenoxy group, a naphthyloxy group, bromine, iodine, chlorine and fluorine are particularly preferred.

As aromatic groups, a phenyl group, a naphthyl group, a thienyl group, a benzothienyl group, an indolyl group, a pyridly group etc. are preferred. As substituting groups of the aromatic groups, a C1–C18 alkyl group, a C1–C18 alkoxy group, a phenoxy group, a naphtyloxy group, bromine, iodine, chlorine, fluorine, a monoalkylamino group, a dialkylamino group, a monoarylamino group, a diarylamino group and a thioalkyl group may be recited. The number of carbon atoms of the alkyl group constituting the thioalkyl group is preferably 1 to 8.

The compound of the formula (I) in which Y=CN can be produced by reacting 1-substituted 2,5-diithienylpyrrole derivative represented by the following formula (II) with 2 or more molar equivalents of tetracyanoethylene in an organic solvent.

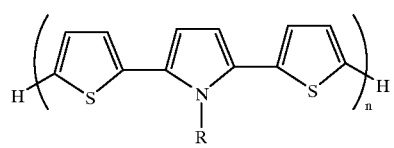

(II)

in which R is a substituted or non-substituted alkyl group, or a substituted or non-substituted aromatic group, and n is an integer of 1 to 3. As to the substituted or non-substituted alkyl group and the substituted or non-substituted aromatic group, those mentioned in connection with the formula (I) may be employed.

Alternatively, the compound according to the present invention can be produced by converting the compound represented by the above formula (II) to a compound of the following formula (III) by an action of a base such as butyl lithium or lithium diisopropylamide, and then reacting the resulting compound with tetracyanoethylene.

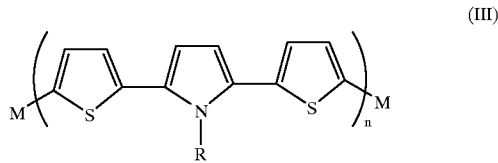

(III)

in which R is a substituted or non-substituted alkyl group, or a substituted or non-substituted aromatic group, and n is an integer of 1 to 3. As to the substituted or non-substituted alkyl group and the substituted or non-substituted aromatic group, those mentioned in connection with the formula (I) may be employed.

A compound of the formula (I) according to the present invention produced by the above method in which R is an allyl group may be substituted by hydrogen through deallylation with a rodium catalyst.

The compound according to the present invention in which Y=H can be easily synthesized by reacting the metal compound represented by obtaining a diformyl product by reacting the above formula (IV) with a derivative of formamide such as dimethylformamide, and reacting the resulting diformyl product with malononitrile in the presence of a base.

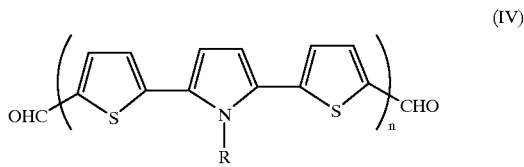

(IV)

in which R is a substituted or non-substituted alkyl group, or a substituted or non-substituted aromatic group, and n is an integer of 1 to 3. As to the substituted or non-substituted alkyl group and the substituted or non-substituted aromatic group, those mentioned in connection with the formula (I) may be employed.

Further, the compound according to the present invention in which one of Ys is a cyano group and the other hydrogen can be easily produced by reacting one mole or more of compound of the following formula (V) containing 2,2-dicyanoethenyl group at one side in a solvent.

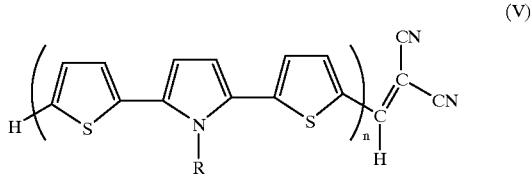

(V)

in which R is a substituted or non-substituted alkyl group, or a substituted or non-substituted aromatic group, and n is an integer of 1 to 3. As to the substituted or non-substituted alkyl group and the substituted or non-substituted aromatic group, those mentioned in connection with the formula (I) may be employed.

EXAMPLES

Hereinafter, examples of the present invention will be explained, but the invention is not limited thereto.

EXAMPLE 1

Into N,N-diethylformamide (10 ml) was dissolved 1-phenyl-2,5-di(2-thienyl)pyrrole (215 mg), and tetracyanoethylene (359 mg: 4 mol equivalents) was added to the solution, which was then stirred at 80° for 24 hours. When the reaction mixture was cooled to room temperature, gold to bronze color crystals of 1-phenyl-2,5-(5-tricyanoeffienyl-2-thienyl)pyrrole were deposited. The crystals were separated by filtration, washed with acetone and chloroform, and dried to give greenish gold crystals (261 mg). Thereafter, the filtrate was added into a saturated aqueous solution of sodium chloride, and the mixture was subjected to extraction with toluene. The organic layer was dried over anhydrous magnesium sulfate, evaporated under reduced pressure, separation by colum chromatography (silica gel, toluene), and recrystallized from acetone, to give gold crystals of 1I-phenyl-2,5-(5-tricyanoethenyl)-2-thienyl)pyrrole (74 mg). The total weight of the product was 335 mg (the total yield of 95%). The product showed the following physical values.

Melting point: not less than 300° C. $^1$H NMR(CDCl$_3$): δ7.09(d, J=4.5Hz, 2H), 7.11(s, 2H), 7.47(d, J=8.7Hz, 2H), 7.71((t, J=8.0Hz, 2H), 7.80(t, J=7.4H, 2H), 7.82(d, J=4.5Hz, 2H) IR absorption spectrum (KBr): 2382, 2218, 1502, 1406, 1379, 1358, 1200, 1120, 778, 696 cm$^{-1}$ UV-visible light absorption spectrum (THF, 3×10$^{-5}$M): λmax (ε/M-1 cm$^{-1}$), 644(63300) Calculated for $C_{28}H_{11}N_7S_2$: C, 66. 0; H, 2.18; N, 19.24%. Measured: C, 65.82; 2.06; N, 19.27%

EXAMPLE 2

Into a mixed solvent of methanol (30ml) and chloroform (10 ml) were dissolved 1-(4-methoxyphenyl)-2,5-bis(5-formyl-2-thienyl)pyrrole (64.5 mg, 0.164 ml) and malononitrile (35.8 mg, 0.381 mmol). After several drops of triethylamine were added to the solution, it was stirred at room temperature for 1 hour. Then, 50 ml of water was added to the solution, which was extracted with chloroform (50 ml×3). The chloroform extracts were collected and subjected to drying over anhydrous magnesium sulfate, and evaporated under reduced pressure. The resulting residue was separated by column chromatography (silica gel, chloroform), and reddish brown crystals of 1-(4-methoxyphenyl)-2,5-bis[(5-(2,2-dicyanoethenyl)-2-thienyl]pyrrole (75.2 mg, 0.154 mmol, 94%) were obtained. The product showed the following physical values.

Melting point: 276.0–276.5° C. $^1$H NMR(CDCl$_3$, 3000MHz): δ3.95(s, 3H), 6.96(s, 2H), 7.02(d, J=4.4Hz, 2H), 7.13(d, J=8.9Hz, 2H), 7.33(d, J=8.8Hz, 2H), 7.50(d, J=4.3Hz, 2H), 7.59(s,2H) IR absorption spectra (KBr): 2220, 1565, 1520, 1460, 1415, 1380, 1340, 1260, 1090, 1075 cm$^{-1}$

EXAMPLE 3

Into N, N-dimethylformamide (50 ml) was dissolved 5,5'-bis [5-(2-thienyl)-1-(4-dodecylphenyl)-2-pyrolyl]-2,2'-dithienyl (350 mg). After tetra-cyanoethylene (94 mg: 2 mol equivalents) was added to the solution, it was stirred at room temperature for 24 hours. A saturated aqueous solution of sodium chloride was added into the reaction mixture, which was then extracted with toluene. The organic layer was dried over anhydrous magnesium sulfate and evaporated under reduced pressure. The resulting solution was separated by column chromatography (silica gel, chloroform), and 5,5'-bis [5-(5-tricyanoethenyl-2-thienyl)-1-(4-dodecylphenyl)-2-pyrolyl])-2,2'-dithienyl was obtained. The weight was 73 mg (the yield of 17%). The product had the following physical values.

Melting point: 206,0–206.5° C. $^1$H NMR(CDC13): δ0.88 (t-like, 6H), 1.20–1.48(m, 36H), 1.68–1.80(m, 4H), 2.77(t-like, 4H), 6.58(d, J=4.0Hz, 2H), 6.72(d, J=4.3Hz, 2H), 6.76(d, J=4.0Hz, 2H), 6.99(d, J=4.5Hz, 2H), 7.05(d, J=4.3Hz, 2H), 7.29(d, J=8.3Hz, 4H), 7.41(d, J=8.3Hz, 2H), 7.73(d, J=4.5Hz, 2H) IR absorption spectrum (KBr): 2205, 1510, 1500, 1495, 1460, 1450, 1420, 1402, 1320,1105 cm$^{-1}$

EXAMPLE 4

Into N, N-dimethylformamide (10 ml) was dissolved 1-(4-methoxylphenyl)-2-[5-(2,2-dicyanoethenyl)-2-thienyl]-5-(2-thienyl)pyrrole (53.7 mg). After tetracyanoethylene (35.3 mg: 2.1 mol equivalents) was added to the solution, it was stirred at room temperature for 21 hours and further at 80° for 18 hours. Into the reaction mixture was added 50 ml of water, which was then extracted with chloroform (50 ml×3). The combined organic layers were subjected to drying over anhydrous magnesium sulfate and condensation under reduced pressure. The resulting residue was separated by column chromatography (silica gel, chloroform), and 1-(methoxyphenyl)-2-[5-(2,2-dicyanoethenyl)-2-thienyl]-5-[5-(tricyanoethenyl)-2-thienyl]pyrrole was obtained (31.8 mg, 0.0618 mmol., 48%). The product had the following physical values.

Melting point: not less than 300° C. $^1$H NMR(CDCl3): δ7.80(d, J=4.8Hz, 1H) 7.61(s, 1H) 7.53(d, J=9.0Hz, 2H) 7.34(d, J=9.0Hz, 2H) 7.20(d, J=4.5Hz, 1H) 7.17(d, J=4.1 Hz, 1H) 7.15(d, J=9.0Hz, 2H) 7.09(d, J=4.6Hz, 1H) 7.00(d, J=4.4Hz, 1H) 3.94(s, 3H) IR absorption spectra (KBr):2220, 1560, 1508, 1495, 1420, 1410, 1360, 1350, 1320, 1100 cm$^{-1}$

EXAMPLES 5 to 22

Compounds in Examples 5 to 22 in Tables 1 and 2 were produced in accordance with the same procedure as that described in Examples 1, 2 or 3. In Tables 1 and 2, a substitutent R, the melting point and physical properties of each of the compounds are shown. In Tables 1 and 2, R, Y and n are those in the following formula (I).

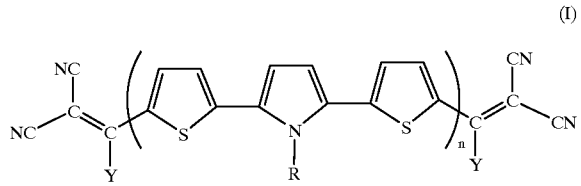

TABLE 1

| No. | R | Y | n | Physical properties |
|---|---|---|---|---|
| 5 | 4-fluorophenyl | CN | 1 | melting point > 300° C., gold crystals (recrystallized from DMF) |
| 6 | 4-chlorophenyl | CN | 1 | melting point > 300° C., gold crystals (recrystallized from DMF) |
| 7 | 4-bromophenyl | CN | 1 | melting point > 300° C., gold crystals (recrystallized from DMF) |
| 8 | 2-bromophenyl | CN | 1 | melting point: 253–254° C., bronze crystals |
| 9 | 2-bromo-4-fluorophenyl | CN | 1 | melting point: 289.8–290.5° C., bronze crystals |
| 10 | 4-cyanophenyl | CN | 1 | melting point > 300° C., gold crystals (recrystallized from DMF) |
| 11 | 4-(methyl)phenyl | CN | 1 | melting point > 300° C., gold crystals (recrystallized from DMF) |

TABLE 1-continued

| No. | R | Y | n | Physical properties |
|---|---|---|---|---|
| 12 | 4-(tert-butylthio)phenyl | CN | 1 | melting point: 257–258.5° C., gold crystals (recrystallized from chlorofrom) or bronze crystals (recrystalized from acetone) |

TABLE 2

| No. | R | Y | n | Physical properties |
|---|---|---|---|---|
| 13 | 4-(diphenylaminophenyl) | CN | 1 | melting point: 221.5–22.5° C., bronze crystals |
| 14 | 4-(dimethylaminophenyl) | CN | 1 | melting point > 300° C., bronze crystals |
| 15 | 4-methoxyphenyl | H | 1 | melting point: 276–276.5° C., dark green solid |
| 16 | 4-n-dodecylphenyl | CN | 1 | melting point: 176.4–177.1° C., reddish purple metallic crystals (recrystallized from DMF) |
| 17 | 4-n-dodecylphenyl | CN | 2 | melting point: 206–206.5° C., bronze crystals |
| 18 | 4-n-tetradecylphenyl | CN | 1 | melting: 162.3–162.9° C., bronze crystals |
| 19 | 4-n-hexanedecylphenyl | CN | 2 | melting point 189–190° C., black solid |
| 20 | 4-n-hexadecylphenyl | CN | 3 | melting point: 183–183.5° C., black solid |
| 21 | isopropyl | CN | 1 | melting point: 224.5–225.5° C., bronze crystals |

TABLE 2-continued

| No. | R | Y | n | Physical properties |
|---|---|---|---|---|
| 22 | cyclohexyl | | CN | 1 | melting point: 254–255° C., bronze crystals |

Since the organic compounds according to the present invention exhibit solubility in organic solvents, their crystals can be easily obtained.

Further, the organic compounds according to the present invention advantageously exhibit stable metallic lusters.

What is claimed is:

1. A 1-substituted 2,5-dithienylpyrrole derivative having the following formula (I).

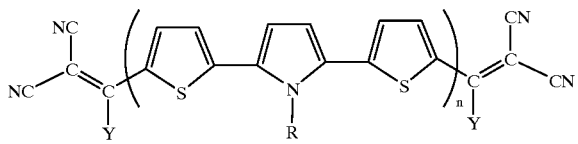

(I)

in which R, is hydrogen, a substituted or non-substituted alkyl group, or a substituted or non-substituted aromatic group, Y is hydrogen or cyano group, provided that one of Ys may be hydrogen and the other may be cyano group, and n is an integer of 1 to 3.

* * * * *